United States Patent [19]

Wideman et al.

[11] Patent Number: 5,684,171
[45] Date of Patent: Nov. 4, 1997

[54] PROCESS FOR THE PREPARATION OF ORGANOSILICON POLYSULFIDE COMPOUNDS

[75] Inventors: Lawson Gibson Wideman, Tallmadge; Theodore Lamson Folk, Cuyahoga Falls; Martin Paul Cohen, Fairlawn, all of Ohio

[73] Assignee: The Goodyear Tire & Rubber Company, Akron, Ohio

[21] Appl. No.: 797,355

[22] Filed: Feb. 11, 1997

[51] Int. Cl.$^6$ .................................. C07F 7/08; C07F 7/18
[52] U.S. Cl. .............................................. 556/427; 544/69
[58] Field of Search ................................ 556/427; 544/69

[56] References Cited

U.S. PATENT DOCUMENTS

| | | | |
|---|---|---|---|
| 5,466,848 | 11/1995 | Childress | 556/427 |
| 5,468,893 | 11/1995 | Parker et al. | 556/427 |
| 5,489,701 | 2/1996 | Childress et al. | 556/427 |
| 5,583,245 | 12/1996 | Parker et al. | 556/427 |

Primary Examiner—Paul F. Shaver
Attorney, Agent, or Firm—Bruce J. Hendricks

[57] ABSTRACT

The present invention relates to a process for the preparation of organosilicon polysulfide compounds. The process involves reacting a mercaptoalkoxysilane with a dithiodimorpholine compound.

11 Claims, No Drawings

PROCESS FOR THE PREPARATION OF ORGANOSILICON POLYSULFIDE COMPOUNDS

BACKGROUND OF THE INVENTION

The present invention relates to a process for the preparation of organosilicon polysulfide compounds. Many organosilicon polysulfides are known adhesion promoters in sulfur-vulcanizable rubber mixtures reinforced with inorganic materials such as glass $SiO_2$, aluminosilicates and carbon black.

U.S. Pat. No. 4,820,751 relates to a rubber composition for use in tires containing certain coupling agents. Amongst the number of coupling agents that are disclosed, unsymmetrical coupling agents containing a benzothiazole moiety is included.

U.S. Pat. Nos. 3,842,111, 3,873,489 and 3,978,103 relate to symmetrical sulfur containing organosilicon compounds. Inclusive amongst such compounds are where the sulfur ranges from $S_2$ to $S_6$.

GB 1,484,909 discloses a process for the preparation of organo trialkoxysilane disulfides. In accordance with the teachings of this reference, mercaptopropyl trimethoxy silane or mercaptopropyl triethoxy silane is reacted with sulfuryl chloride in an inert solvent at temperatures of from 0° to 100°. The disulfide is then obtained by fractional distillation. The yields of desired product range in the neighborhood of 63 to 65 percent of theoretical.

U.S. Pat. No. 3,842,111 discloses a method for the preparation of organosilicon disulfide compounds by oxidizing mercaptoalkoxysilanes. Representative oxidizing agents include oxygen, chlorine, halogens of atomic weight 35 to 127, nitric oxide, sulfuryl chloride and sulfoxides.

Generally speaking, organosilicon polysulfide compounds are very expensive and, with the increasing interest in silica-reinforced vulcanizable rubber, more cost-efficient methods of preparing these compounds are needed.

U.S. Pat. No. 4,002,594 relates to rubber vulcanizates reinforced with silica. The patent discloses that the addition of a mercapto-type coupling agent, such as mercaptopropyltrimethoxysilane, hastens curing and strengthens adhesion between the rubber polymer and the silica but tends to cause scorch. The further addition of a thiomorpholine compound such as dithiodimorpholine retards scorch and improves abrasion resistance.

SUMMARY OF THE INVENTION

The present invention relates to a process for the preparation of organosilicon polysulfide compounds. The present invention may be used to prepare symmetrical organosilicon polysulfide compounds of the formula:

$$Z\text{—}R^1\text{—}S_n\text{—}R_1\text{—}Z \qquad \text{I}$$

wherein Z is selected from the group consisting of

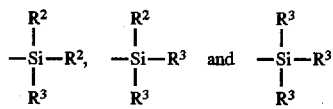

wherein $R^1$ is selected from the group consisting of a substituted or unsubstituted alkylene group having a total of 1 to 18 carbon atoms and a substituted or unsubstituted arylene group having a total of 6 to 12 carbon atoms; n is an integer of from 2 to 8; $R^2$ may be the same or different and is independently selected from the group consisting of an alkyl group having 1 to 18 carbons and phenyl; and $R^3$ may be the same or different and is independently selected from the group consisting of alkoxy groups having 1 to 8 carbon atoms and cycloalkoxy groups with 5 to 8 carbon atoms.

DETAILED DESCRIPTION OF THE INVENTION

There is disclosed a process for the preparation of organosilicon polysulfide compounds comprising reacting (a) the dithiodimorpholine compound of the formula

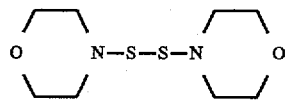

with (b) mercaptosilane compound of the formula $$Z\text{—}R^1\text{—}SH \qquad \text{III}$$

wherein Z is selected from the group consisting of

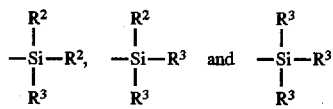

wherein $R^1$ is selected from the group consisting of a substituted or unsubstituted alkylene group having a total of 1 to 18 carbon atoms and a substituted or unsubstituted arylene group having a total of 6 to 12 carbon atoms; $R^2$ may be the same or different and is independently selected from the group consisting of an alkyl group having 1 to 18 carbons and phenyl; and $R^3$ may be the same or different and is independently selected from the group consisting of alkoxy groups having 1 to 8 carbon atoms and cycloalkoxy groups with 5 to 8 carbon atoms.

The present invention relates to a process for the preparation of organosilicon polysulfide compounds. Representative organosilicon polysulfide compounds of formula I where n is 2 which may be prepared in accordance with the present invention include 2,2'-bis(trimethoxysilylethyl) disulfide; 3,3'-bis(trimethoxysilylpropyl) disulfide; 3,3'-bis(triethoxysilylpropyl) disulfide; 2,2'-bis(triethoxysilylethyl) disulfide; 2,2'-bis(tripropoxysilylethyl) disulfide; 2,2'-bis(tri-sec-butoxysilylethyl) disulfide; 2,2'-bis(tri-t-butoxysilylethyl) disulfide; 3,3'-bis(triisopropoxysilylpropyl) disulfide; 3,3'-bis(trioctoxysilylpropyl) disulfide; 2,2'-bis[tri(2-ethylhexoxy)silylethyl] disulfide; 2,2'-bis(dimethoxy ethoxysilylethyl) disulfide; 3,3'-bis(methoxyethoxypropoxysilylpropyl) disulfide; 3,3'-bis(dimethoxymethylsilylpropyl) disulfide; 3,3'-bis(methoxy dimethylsilylpropyl) disulfide; 3,3'-bis(diethoxymethylsilylpropyl) disulfide, 3,3'-bis(ethoxy dimethylsilylpropyl) disulfide, 3,3'-bis(cyclohexoxy dimethylsilylpropyl) disulfide; 4,4'-bis(trimethoxysilylbutyl) disulfide; 3,3'-bis(trimethoxysilyl-3-methylpropyl) disulfide; 3,3'-bis(tripropoxysilyl-3-methylpropyl) disulfide; 3,3'bis(dimethoxy methylsilyl-3-ethylpropyl) disulfide; 3,3'-bis(trimethoxysilyl-2-methylpropyl) disulfide; 3,3'-bis(dimethoxyphenylsilyl-2-methylpropyl) disulfide; 3,3'-bis(trimethoxysilylcyclohexyl) disulfide; 12,12'-bis(trimethoxysilyldodecyl) disulfide;

12,12'-bis(triethoxysilyldodecyl) disulfide; 18,18'-bis(trimethoxysilyloctadecyl) disulfide; 18,18'-bis(methoxydimethylsilyloctadecyl) disulfide; 2,2'-bis(trimethoxysilyl-2-methylethyl) disulfide; 2,2'-bis(tripropoxysilyl-2-methylethyl) disulfide; 2,2'-bis(trioctoxysilyl-2-methylethyl) disulfide; 2,2'-bis(trimethoxysilyl-phenyl) disulfide; 2,2'-bis(triethoxysilyl-phenyl) disulfide; 2,2'-bis(trimethoxysilyl-tolyl) disulfide; 2,2'-bis(triethoxysilyl-tolyl) disulfide; 2,2'-bis(trimethoxysilyl-methyl tolyl) disulfide; 2,2'-bis(triethoxysilyl-methyl tolyl) disulfide; 2,2'-bis(trimethoxysilyl-ethyl phenyl) disulfide; 2,2'-bis(triethoxysilyl-ethyl phenyl) disulfide; 2,2'-bis(trimethoxysilyl-ethyl tolyl) disulfide; 2,2'-bis(triethoxysilyl-ethyl tolyl) disulfide; 3,3'-bis(trimethoxysilyl-propyl phenyl) disulfide; 3,3'-bis(triethoxysilyl-propyl phenyl) disulfide; 3,3'-bis(trimethoxysilyl-propyl tolyl) disulfide; and 3,3'-bis(triethoxysilyl-propyl tolyl) disulfide.

Representative organosilicon polysulfide compounds of formula I where n is 3 which may be prepared in accordance with the present invention include 2,2'-bis(trimethoxysilylethyl) trisulfide; 3,3'-bis(trimethoxysilylpropyl) trisulfide; 3,3'-bis(triethoxysilylpropyl) trisulfide; 2,2'-bis(tripropoxysilylethyl) trisulfide; 2,2'-bis(triethoxysilylethyl) trisulfide; 2,2'-bis(tri-sec-butoxysilylethyl) trisulfide; 2,2'-bis(tri-t-butoxyethyl) trisulfide; 3,3'-bis(triisopropoxysilylpropyl) trisulfide; 3,3'-bis(trioctoxysilylpropyl) trisulfide; 2,2'-bis[tri(2-ethylhexoxy)silylethyl] trisulfide; 2,2'-bis(dimethoxy ethoxysilylethyl) trisulfide; 3,3'-bis(methoxyethoxypropoxysilylpropyl) trisulfide; 3,3'-bis(dimethoxymethylsilylpropyl) trisulfide; 3,3'-bis(methoxy dimethylsilylpropyl) trisulfide; 3,3'-bis(diethoxymethylsilylpropyl) trisulfide; 3,3'-bis(ethoxydimethylsilylpropyl) trisulfide; 3,3'-bis(cyclohexoxy dimethylsilylpropyl) trisulfide; 4,4'-bis(trimethoxysilylbutyl) trisulfide; 3,3'-bis(trimethoxysilyl-3-methylpropyl) trisulfide; 3,3'-bis(tripropoxysilyl-3-methylpropyl) trisulfide; 3,3'-bis(dimethoxy methylsilyl-3-ethylpropyl) trisulfide; 3,3'-bis(trimethoxysilyl-2-methylpropyl) trisulfide; 3,3'-bis(dimethoxyphenylsilyl-2-methylpropyl) trisulfide; 3,3'-bis(trimethoxysilylcyclohexyl) trisulfide; 12,12'-bis(trimethoxysilyldodecyl) trisulfide; 12,12'-bis(triethoxysilyldodecyl) trisulfide; 18,18'-bis(trimethoxysilyloctadecyl) trisulfide; 18,18'-bis(methoxydimethylsilyloctadecyl) trisulfide; 2,2'-bis(trimethoxysilyl-2-methylethyl) trisulfide; 2,2'-bis(tripropoxysilyl-2-methylethyl) trisulfide; 2,2'-bis(trioctoxysilyl-2-methylethyl) trisulfide; 2,2'-bis(trimethoxysilyl-phenyl) trisulfide; 2,2'-bis(triethoxysilyl-phenyl) trisulfide; 2,2'-bis(trimethoxysilyl-tolyl)trisulfide; 2,2'-bis(triethoxysilyl-tolyl)trisulfide; 2,2'-bis(trimethoxysilyl-methyl tolyl) trisulfide; 2,2'-bis(triethoxysilyl-methyl tolyl) trisulfide; 2,2'-bis(trimethoxysilyl-ethyl phenyl) trisulfide; 2,2'-bis(triethoxysilyl-ethyl phenyl) trisulfide; 2,2'-bis(trimethoxysilyl-ethyl tolyl) trisulfide; 2,2'-bis(triethoxysilyl-ethyl tolyl) trisulfide; 3,3'-bis(trimethoxysilyl-propyl phenyl) trisulfide; 3,3'-bis(triethoxysilyl-propyl phenyl) trisulfide; 3,3'-bis(trimethoxysilyl-propyl tolyl) trisulfide; and 3,3'-bis(triethoxysilyl-propyl tolyl) trisulfide.

Representative organosilicon polysulfide compounds of formula I where n is 4 which may be prepared in accordance with the present invention include 2,2'-bis(trimethoxysilylethyl) tetrasulfide; 3,3'-bis(trimethoxysilylpropyl) tetrasulfide; 3,3'-bis(triethoxysilylpropyl) tetrasulfide; 2,2'-bis(tripropoxysilylethyl) tetrasulfide; 2,2'-bis(triethoxysilylethyl) tetrasulfide; 2,2'-bis(tri-sec-butoxysilylethyl) tetrasulfide; 2,2'-bis(tri-t-butoxyethyl) tetrasulfide; 3,3'-bis(triisopropoxysilylpropyl) tetrasulfide; 3,3'-bis(trioctoxysilylpropyl) tetrasulfide; 2,2'-bis[tri(2-ethylhexoxy)silylethyl] tetrasulfide; 2,2'-bis(dimethoxy ethoxysilylethyl) tetrasulfide; 3,3'-bis(methoxyethoxypropoxysilylpropyl) tetrasulfide; 3,3'-bis(dimethoxymethylsilylpropyl) tetrasulfide; 3,3'-bis(methoxy dimethylsilylpropyl) tetrasulfide; 3,3'-bis(diethoxymethylsilylpropyl) tetrasulfide; 3,3'-bis(ethoxydimethylsilylpropyl) tetrasulfide; 3,3'-bis(cyclohexoxy dimethylsilylpropyl) tetrasulfide; 4,4'-bis(trimethoxysilylbutyl) tetrasulfide; 3,3'-bis(trimethoxysilyl-3-methylpropyl) tetrasulfide; 3,3'-bis(tripropoxysilyl-3-methylpropyl) tetrasulfide; 3,3'-bis(dimethoxymethylsilyl-3-ethylpropyl) tetrasulfide; 3,3'-bis(trimethoxysilyl-2-methylpropyl) tetrasulfide; 3,3'-bis(dimethoxyphenylsilyl-2-methylpropyl) tetrasulfide; 3,3'-bis(trimethoxysilylcyclohexyl) tetrasulfide; 12,12'-bis(trimethoxysilyldodecyl) tetrasulfide; 12,12'-bis(triethoxysilyldodecyl) tetrasulfide; 18,18'-bis(trimethoxysilyloctadecyl) tetrasulfide; 18,18'-bis(methoxydimethylsilyloctadecyl) tetrasulfide; 2,2'-bis(trimethoxysilyl-2-methylethyl) tetrasulfide; 2,2'-bis(tripropoxysilyl-2-methylethyl) tetrasulfide; 2,2'-bis(trioctoxysilyl-2-methylethyl) tetrasulfide; 2,2'-bis(trimethoxysilyl-phenyl) tetrasulfide; 2,2'-bis(triethoxysilyl-phenyl) tetrasulfide; 2,2'-bis(trimethoxysilyl-tolyl) tetrasulfide; 2,2'-bis(triethoxysilyl-tolyl) tetrasulfide; 2,2'-bis(trimethoxysilyl-methyl tolyl) tetrasulfide; 2,2'-bis(triethoxysilyl-methyl tolyl) tetrasulfide; 2,2'-bis(trimethoxysilyl-ethyl phenyl) tetrasulfide; 2,2'-bis(triethoxysilyl-ethyl phenyl) tetrasulfide; 2,2'-bis(trimethoxysilyl-ethyl tolyl) tetrasulfide; 2,2'-bis(triethoxysilyl-ethyl tolyl) tetrasulfide; 3,3'-bis(trimethoxysilyl-propyl phenyl) tetrasulfide; 3,3'-bis(triethoxysilyl-propyl phenyl) tetrasulfide; 3,3'-bis(trimethoxysilyl-propyl tolyl) tetrasulfide; and 3,3'-bis(triethoxysilyl-propyl tolyl) tetrasulfide.

Representative of organosilicon polysulfide compounds of formula I when n is 5 which may be prepared in accordance with the present invention include 2,2'-bis(trimethoxysilylethyl) pentasulfide; 3,3'-bis(trimethoxysilylpropyl) pentasulfide; 3,3'-bis(triethoxysilylpropyl) pentasulfide; 2,2'-bis(tripropoxysilylethyl) pentasulfide; 2,2'-bis(triethoxysilylethyl) pentasulfide; 2,2'-bis(tri-sec-butoxysilylethyl) pentasulfide; 2,2'-bis(tri-t-butoxyethyl) pentasulfide; 3,3'-bis(triisopropoxysilylpropyl) pentasulfide; 3,3'-bis(trioctoxysilylpropyl) pentasulfide; 2,2'-bis[tri(2-ethylhexoxy) silylethyl] pentasulfide; 2,2'-bis(dimethoxy ethoxysilylethyl) pentasulfide; 3,3'-bis(methoxyethoxypropoxysilylpropyl) pentasulfide; 3,3'-bis(dimethoxymethylsilylpropyl) pentasulfide; 3,3'-bis(methoxy dimethylsilylpropyl) pentasulfide; 3,3'-bis(diethoxymethylsilylpropyl) pentasulfide; 3,3'-bis(ethoxydimethylsilylpropyl) pentasulfide; 3,3'-bis(cyclohexoxy dimethylsilylpropyl) pentasulfide; 4,4'-bis(trimethoxysilylbutyl) pentasulfide; 3,3'-bis(trimethoxysilyl-3-methylpropyl) pentasulfide; 3,3'-bis(tripropoxysilyl-3-methylpropyl) pentasulfide; 3,3'-bis(dimethoxy methylsilyl-3-ethylpropyl) pentasulfide; 3,3'-bis(trimethoxysilyl-2-methylpropyl) pentasulfide; 3,3'-bis (dimethoxyphenylsilyl-2-methylpropyl) pentasulfide; 3,3'-bis(trimethoxysilylcyclohexyl) pentasulfide; 12,12'-bis(trimethoxysilyldodecyl) pentasulfide; 12,12'-bis(triethoxysilyldodecyl) pentasulfide; 18,18'-bis(trimethoxysilyloctadecyl) pentasulfide; 18,18'-bis(methoxydimethylsilyloctadecyl) pentasulfide; 2,2'-bis(trimethoxysilyl-2-methylethyl) pentasulfide; 2,2'-bis(tripropoxysilyl-2-methylethyl) pentasulfide; 2,2'-bis(trioctoxysilyl-2-methylethyl) pentasulfide; 2,2'-bis(trimethoxysilyl-phenyl) pentasulfide; 2,2'-bis(triethoxysilyl-phenyl) pentasulfide; 2,2'-bis(trimethoxysilyl-tolyl) pentasulfide; 2,2'-bis(triethoxysilyl-tolyl) pentasulfide; 2,2'-bis(trimethoxysilyl-methyl tolyl) pentasulfide; 2,2'-bis(triethoxysilyl-methyl tolyl) pentasulfide; 2,2'-bis(trimethoxysilyl-ethyl phenyl) pentasulfide; 2,2'-bis(triethoxysilyl-ethyl phenyl) pentasulfide; 2,2'-bis(trimethoxysilyl-ethyl tolyl) pentasulfide; 2,2'-bis(triethoxysilyl-ethyl tolyl) pentasulfide; 3,3'-bis(trimethoxysilyl-propyl phenyl) pentasulfide; 3,3'-bis(triethoxysilyl-propyl phenyl) pentasulfide; 3,3'-bis(trimethoxysilyl-propyl tolyl) pentasulfide; and 3,3'-bis(triethoxysilyl-propyl tolyl) pentasulfide.

Representative of organosilicon polysulfide compounds of formula I where n is 6 which may be prepared in accordance with the present invention include 2,2'-bis(trimethoxysilylethyl) hexasulfide; 3,3'-bis(trimethoxysilylpropyl) hexasulfide; 3,3'-bis(triethoxysilylpropyl) hexasulfide; 2,2'-bis(tripropoxysilylethyl) hexasulfide; 2,2'-bis(triethoxysilylethyl) hexasulfide; 2,2'-bis(tri-sec-butoxysilylethyl) hexasulfide; 2,2'-bis(tri-t-butoxyethyl) hexasulfide; 3,3'-bis(triisopropoxysilylpropyl) hexasulfide; 3,3'-bis(trioctoxysilylpropyl) hexasulfide; 2,2'-bis[tri(2-ethylhexoxy)silylethyl] hexasulfide; 2,2'-bis(dimethoxy ethoxysilylethyl) hexasulfide; 3,3'-bis(methoxyethoxypropoxysilylpropyl) hexasulfide; 3,3'-bis(dimethoxymethylsilylpropyl) hexasulfide; 3,3'-bis(methoxy dimethylsilylpropyl) hexasulfide; 3,3'-bis(diethoxymethylsilylpropyl) hexasulfide; 3,3'-bis(ethoxydimethylsilylpropyl) hexasulfide; 3,3'-bis(cyclohexoxy dimethylsilylpropyl) hexasulfide; 4,4'-bis(trimethoxysilylbutyl) hexasulfide; 3,3'-bis(trimethoxysilyl-3-methylpropyl) hexasulfide; 3,3'-bis(tripropoxysilyl-3-methylpropyl) hexasulfide; 3,3'-bis(dimethoxy methylsilyl-3-ethylpropyl) hexasulfide; 3,3'-bis(trimethoxysilyl-2-methylpropyl) hexasulfide; 3,3'-bis(dimethoxyphenylsilyl-2-methylpropyl) hexasulfide; 3,3'-bis(trimethoxysilylcyclohexyl) hexasulfide; 12,12'-bis(trimethoxysilyldodecyl) hexasulfide; 12,12'-bis(triethoxysilyldodecyl) hexasulfide; 18,18'-bis(trimethoxysilyloctadecyl) hexasulfide; 18,18'-bis(methoxydimethylsilyloctadecyl) hexasulfide; 2,2'-bis(trimethoxysilyl-2-methylethyl) hexasulfide; 2,2'-bis(tripropoxysilyl-2-methylethyl) hexasulfide; 2,2'-bis(trioctoxysilyl-2-methylethyl) hexasulfide; 2,2'-bis(trimethoxysilyl-phenyl) hexasulfide; 2,2'-bis(triethoxysilyl-phenyl) hexasulfide; 2,2'-bis(trimethoxysilyl-tolyl) hexasulfide; 2,2'-bis(triethoxysilyl-tolyl) hexasulfide; 2,2'-bis(trimethoxysilyl-methyl tolyl) hexasulfide; 2,2'-bis(triethoxysilyl-methyl tolyl) hexasulfide; 2,2'-bis(trimethoxysilyl-ethyl phenyl) hexasulfide; 2,2'-bis(triethoxysilyl-ethyl phenyl) hexasulfide; 2,2'-bis(trimethoxysilyl-ethyl tolyl) hexasulfide; 2,2'-bis(triethoxysilyl-ethyl tolyl) hexasulfide; 3,3'-bis(trimethoxysilyl-propyl phenyl) hexasulfide; 3,3'-bis(triethoxysilyl-propyl phenyl) hexasulfide; 3,3'-bis(trimethoxysilyl-propyl tolyl) hexasulfide; and 3,3'-bis(triethoxysilyl-propyl tolyl) hexasulfide.

Representative organosilicon polysulfide compounds of formula I where n is 7 which may be prepared in accordance with the present invention include 2,2'-bis(trimethoxysilylethyl) heptasulfide; 3,3'-bis(trimethoxysilylpropyl) heptasulfide; 3,3'-bis(triethoxysilylpropyl) heptasulfide; 2,2'-bis(tripropoxysilylethyl) heptasulfide; 2,2'-bis(triethoxysilylethyl) heptasulfide; 2,2'-bis(tri-sec-butoxysilylethyl) heptasulfide; 2,2'-bis(tri-t-butoxyethyl) heptasulfide; 3,3'-bis(triisopropoxysilylpropyl) heptasulfide; 3,3'-bis(trioctoxysilylpropyl) heptasulfide; 2,2'-bis[tri(2-ethylhexoxy)silylethyl] heptasulfide; 2,2'-bis(dimethoxy ethoxysilylethyl) heptasulfide; 3,3'-bis(methoxyethoxypropoxysilylpropyl) heptasulfide; 3,3'-bis(dimethoxymethylsilylpropyl) heptasulfide; 3,3'-bis(methoxy dimethylsilylpropyl) heptasulfide; 3,3'-bis(diethoxymethylsilylpropyl) heptasulfide; 3,3'-bis(ethoxydimethylsilylpropyl) heptasulfide; 3,3'-bis(cyclohexoxy dimethylsilylpropyl) heptasulfide; 4,4'-bis(trimethoxysilylbutyl) heptasulfide; 3,3'-bis(trimethoxysilyl-3-methylpropyl) heptasulfide; 3,3'-bis(tripropoxysilyl-3-methylpropyl) heptasulfide; 3,3'-bis(dimethoxy methylsilyl-3-ethylpropyl) heptasulfide; 3,3'-bis(trimethoxysilyl-2-methylpropyl) heptasulfide; 3,3'-bis(dimethoxyphenylsilyl-2-methylpropyl) heptasulfide; 3,3'-bis(trimethoxysilylcyclohexyl) heptasulfide; 12,12'-bis(trimethoxysilyldodecyl) heptasulfide; 12,12'-bis(triethoxysilyldodecyl) heptasulfide; 18,18'-bis(trimethoxysilyloctadecyl) heptasulfide; 18,18'-bis(methoxydimethylsilyloctadecyl) heptasulfide; 2,2'-bis(trimethoxysilyl-2-methylethyl) heptasulfide; 2,2'-bis(tripropoxysilyl-2-methylethyl) heptasulfide; 2,2'-bis(trioctoxysilyl-2-methylethyl) heptasulfide; 2,2'-bis(trimethoxysilyl-phenyl) heptasulfide; 2,2'-bis(triethoxysilyl-phenyl) heptasulfide; 2,2'-bis(trimethoxysilyl-tolyl)heptasulfide; 2,2'-bis(triethoxysilyl-tolyl)heptasulfide; 2,2'-bis(trimethoxysilyl-methyl tolyl) heptasulfide; 2,2'-bis(triethoxysilyl-methyl tolyl) heptasulfide; 2,2'-bis(trimethoxysilyl-ethyl phenyl) heptasulfide; 2,2'-bis(triethoxysilyl-ethyl phenyl) heptasulfide; 2,2'-bis(trimethoxysilyl-ethyl tolyl) heptasulfide; 2,2'-bis(triethoxysilyl-ethyl tolyl) heptasulfide; 3,3'-bis(trimethoxysilyl-propyl phenyl) heptasulfide; 3,3'-bis(triethoxysilyl-propyl phenyl) heptasulfide; 3,3'-bis(trimethoxysilyl-propyl tolyl) heptasulfide; and 3,3'-bis(triethoxysilyl-propyl tolyl) heptasulfide.

Representative organosilicon polysulfide compounds of formula I where n is 8 which may be prepared in accordance with the present invention include 2,2'-bis(trimethoxysilylethyl) octasulfide; 3,3'-bis(trimethoxysilylpropyl) octasulfide; 3,3'-bis(triethoxysilylpropyl) octasulfide; 2,2'-bis(tripropoxysilylethyl) octasulfide; 2,2'-bis(triethoxysilylethyl) octasulfide; 2,2'-bis(tri-sec-butoxysilylethyl) octasulfide; 2,2'-bis(tri-t-butoxyethyl) octasulfide; 3,3'-bis(triisopropoxysilylpropyl) octasulfide; 3,3'-bis(trioctoxysilylpropyl) octasulfide; 2,2'-bis[tri(2-ethylhexoxy) silylethyl] octasulfide; 2,2'-bis(dimethoxy ethoxysilylethyl) octasulfide; 3,3'-bis(methoxyethoxypropoxysilylpropyl) octasulfide; 3,3'-bis(dimethoxymethylsilylpropyl) octasulfide; 3,3'-bis(methoxy dimethylsilylpropyl) octasulfide; 3,3'-bis(diethoxymethylsilylpropyl) octasulfide; 3,3'-bis(ethoxydimethylsilylpropyl) octasulfide; 3,3'-bis(cyclohexoxy dimethylsilylpropyl) octasulfide; 4,4'-bis(trimethoxysilylbutyl) octasulfide; 3,3'-bis(trimethoxysilyl-3-methylpropyl) octasulfide; 3,3'-bis(tripropoxysilyl-3- methylpropyl) octasulfide; 3,3'-bis(dimethoxy methylsilyl-3-ethylpropyl) octasulfide; 3,3'-bis(trimethoxysilyl-2-methylpropyl) octasulfide; 3,3'-bis(dimethoxyphenylsilyl-2-methylpropyl) octasulfide; 3,3'-bis (trimethoxysilylcyclohexyl) octasulfide; 12,12'-bis (trimethoxysilyldodecyl) octasulfide; 12,12'-bis (triethoxysilyldodecyl) octasulfide; 18,18'-bis (trimethoxysilyloctadecyl) octasulfide; 18,18'-bis (methoxydimethylsilyloctadecyl) octasulfide; 2,2'-bis (trimethoxysilyl-2-methylethyl) octasulfide; 2,2'-bis (tripropoxysilyl-2-methylethyl) octasulfide; 2,2'-bis (trioctoxysilyl-2-methylethyl) octasulfide; 2,2'-bis (trimethoxysilyl-phenyl) octasulfide; 2,2'-bis(triethoxysilyl-phenyl) octasulfide; 2,2'-bis(trimethoxysilyl-tolyl) octasulfide; 2,2'-bis(triethoxysilyl-tolyl) octasulfide; 2,2'-bis (trimethoxysilyl-methyl tolyl) octasulfide; 2,2'-bis (triethoxysilyl-methyl tolyl) octasulfide; 2,2'-bis (trimethoxysilyl-ethyl phenyl) octasulfide; 2,2'-bis (triethoxysilyl-ethyl phenyl) octasulfide; 2,2'-bis (trimethoxysilyl-ethyl tolyl) octasulfide; 2,2'-bis (triethoxysilyl-ethyl tolyl) octasulfide; 3,3'-bis (trimethoxysilyl-propyl phenyl) octasulfide; 3,3'-bis (triethoxysilyl-propyl phenyl) octasulfide; 3,3'-bis (trimethoxysilyl-propyl tolyl) octasulfide; and 3,3'-bis (triethoxysilyl-propyl tolyl) octasulfide.

With reference to formula I, preferably $R^1$ is an alkylene group having 2 to 3 carbon atoms, Z is

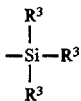

and $R^3$ is an alkoxy group having from 1 to 3 carbon atoms.

The desired products are prepared by reacting the dithiodimorpholine compound of formula II with a mercaptosilane compound of formula III. Representative examples of compounds of formula III include 2-mercaptoethyl trimethoxysilane, 3-mercaptopropyl trimethoxysilane, 3-mercaptopropyl triethoxysilane, 2-mercaptopropyl triethoxysilane, 2-mercaptoethyl tripropoxysilane, 2-mercaptoethyl tri sec-butoxysilane, 3-mercaptopropyl tri-t-butoxysilane, 3-mercaptopropyl triisopropoxysilane; 3-mercaptopropyl trioctoxysilane, 2-mercaptoethyl tri(2-ethylhexoxy)silane, 2-mercaptoethyl dimethoxyethoxysilane, 3-mercaptopropyl methoxyethoxypropoxysilane, 3-mercaptopropyl dimethoxy methylsilane, 3-mercaptopropyl methoxydimethylsilane, 3-mercaptopropyl ethoxydimethylsilane, 3-mercaptopropyl diethoxy methylsilane, 3-mercaptopropyl cyclohexoxydimethylsilane, 4-mercaptobutyl trimethoxysilane, 3-mercapto-3-methylpropyltrimethoxysilane, 3-mercapto-3-methylpropyltripropoxysilane, 3-mercapto-3-ethylpropyldimethoxymethylsilane, 3-mercapto-2-methylpropyl trimethoxysilane, 3-mercapto-2-methylpropyl dimethoxyphenylsilane, 3-mercaptocyclohexyltrimethoxysilane, 12-mercaptododecyl trimethoxysilane, 12-mercaptododecyl triethoxysilane, 18-mercaptooctadecyl trimethoxysilane, 18-mercaptooctadecyl methoxydimethylsilane, 2-mercapto-2-methylethyltripropoxysilane, 2-mercapto-2-methylethyltrioctoxysilane, 2-mercaptophenyl trimethoxysilane, 2-mercaptophenyl triethoxysilane; 2-mercaptotolyl trimethoxysilane; 2-mercaptotolyl triethoxysilane; 2-mercaptoethylphenyl trimethoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

With reference to formula III, preferably Z is

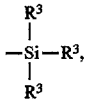

$R^3$ is an alkoxy group having from 1 to 3 carbon atoms and $R^1$ is an alkylene group having 2 to 3 carbon atoms.

The molar ratio of the compound of formula II to the compound of formula III may range from 1:5 to 5:1. Preferably, the molar ratio ranges from 1:3 to 3:1 with a range of from 1:1 to 1:2 being particularly preferred.

Preferably, the reaction is conducted in the absence of water because the presence of an alkoxysilane moiety may be hydrolysed by contact with water.

The reaction of the present invention may be conducted in the presence of an organic solvent. Suitable solvents which may be used include chloroform, dichloromethane, carbon tetrachloride, hexane, heptane, cyclohexane, xylene, benzene, dichloroethylene, trichtoroethylene, dioxane, diisopropyl ether, tetrahydrofuran and toluene. As indicated above, care should be exercised to avoid the presence of water during the reaction. Therefore, none of the above solvent should contain any appreciable levels of water. Preferably, the organic solvent is chloroform, heptane, cyclohexane, xylene and toluene.

The reaction may be conducted over a variety of temperatures. Generally speaking, the reaction is conducted in a temperature ranging from 10° C. to 140° C. Preferably, the reaction is conducted at a temperature ranging from 20° C. to 90° C.

The process of the present invention may be conducted at a variety of pressures. Generally speaking, however, the reaction is conducted at a pressure ranging from 0.096 to 4.83 kg/cm$^2$.

EXAMPLE 1

Preparation of Organosilicon Polysulfide Compounds

A 1-quart reactor was charged with 47.2 g (0.20 mole) of 4,4'-dithiodimorpholine and 47.6 g (0.20 mole) of 3-mercaptopropyltriethoxysilane in 400 ml of toluene. The reactor was flushed with nitrogen and stirred briefly until a solution was attained at room temperature. The reaction mixture was allowed to stand for 24 hours at room temperature before the toluene solvent and morpholine side-product were distilled away under reduced pressure. The resulting liquid-dithiomorpholine mixture was separated by filtering to give 33.3 grams of the liquid compound of formula I where each $R^1$ was an unsubstituted alkylene group having a total of 3 carbon atoms, each Z is of the formula:

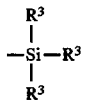

each $R^3$ was an alkoxy group having 2 carbon atoms and, as shown by Mass Spectrometry analysis, the area percent distribution of Sn polysulfide was as follows:

| n | area % |
|---|---|
| $S_2$ | 17 |
| $S_3$ | 33 |
| $S_4$ | 26 |
| $S_5$ | 18 |
| $S_6$ | 5 |
| $S_7$ | 1 | which represents 95 percent of the observed reaction product.

EXAMPLE 2

Preparation of Organosilicon Polysulfide Compounds

A reaction was carried out under the conditions of example 1 except 94.4 g (0.40 mole) of 4,4'dithiodimorpholine and 104.8 g (0.44 mole) of 3-mercaptopropyltriethoxysilane were added to the reactor in 800 ml of toluene. Work-up gave 67.5 g of the compound of formula I where each $R^1$ was an unsubstituted alkylene group having a total of 3 carbon atoms, each Z is of the formula:

each $R^3$ was an alkoxy group having 2 carbon atoms and, as shown by Mass Spectrometry analysis, the area percent distribution of Sn polysulfide was as follows:

| n | area % |
|---|---|
| $S_2$ | 14 |
| $S_3$ | 33 |
| $S_4$ | 30 |
| $S_5$ | 15 |
| $S_6$ | 6 |
| $S_7$ | 2 | which represents 99 percent of the observed reaction product.

What is claimed is:

1. A process for the preparation of organosilicon polysulfide compounds comprising reacting (a) a dithiodimorpholine compound of the formula

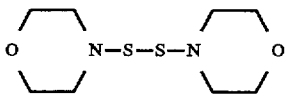   II with (b) mercaptosilane compound of the formula

   III wherein Z is selected from the group consisting of

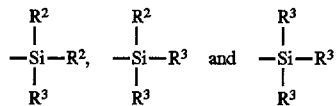

wherein $R^1$ is selected from the group consisting of a substituted or unsubstituted alkylene group having a total of 1 to 18 carbon atoms and a substituted or unsubstituted arylene group having a total of 6 to 12 carbon atoms; $R^2$ may be the same or different and is independently selected from the group consisting of an alkyl group having 1 to 18 carbons and phenyl; and $R^3$ may be the same or different and is independently selected from the group consisting of alkoxy groups having 1 to 8 carbon atoms and cycloalkoxy groups with 5 to 8 carbon atoms.

2. The process of claim 1 wherein said reaction is in the absence of water and in the presence of an organic solvent selected from the group consisting of chloroform, dichloromethane, carbon tetrachloride, hexane, heptane, cyclohexane, xylene, benzene, dichloroethylene, trichloroethylene, dioxane, diisopropyl ether, tetrahydrofuran and toluene.

3. The process of claim 1 wherein Z is

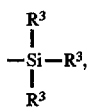

$R^3$ selected from the group consisting of alkoxy groups having 1 to 3 carbon atoms and $R^1$ is an alkylene group having 2 to 3 carbon atoms.

4. The process of claim 1 wherein the molar ratio of the compound of formula II to the compound of formula III ranges from 1:5 to 5:1.

5. The process of claim 4 wherein the molar ratio of the compound of formula II to the compound of formula III ranges from 1:3 to 3:1.

6. The process of claim 1 wherein said organosilicon polysulfide compounds are of the formula:

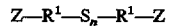   I wherein Z is selected from the group consisting of

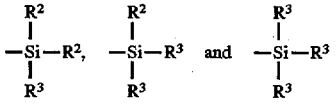

wherein $R^1$ is selected from the group consisting of a substituted or unsubstituted alkylene group having a total of 1 to 18 carbon atoms and a substituted or unsubstituted arylene group having a total of 6 to 12 carbon atoms; and n is an integer of from 2 to 8; $R^2$ may be the same or different and is independently selected from the group consisting of an alkyl group having 1 to 18 carbons and phenyl; and $R^3$ may be the same or different and is independently selected from the group consisting of alkoxy groups having 1 to 8 carbon atoms and cycloalkoxy groups with 5 to 8 carbon atoms.

7. The process of claim 1 wherein said mercaptosilane compound of formula III is selected from a group consisting of 2-mercaptoethyl trimethoxysilane, 3-mercaptopropyl trimethoxysilane, 2-mercaptopropyl triethoxysilane, 3-mercaptopropyl triethoxysilane, 2-mercaptoethyl tripropoxysilane, 2-mercaptoethyl tri sec-butoxysilane, 3-mercaptopropyl tri-t-butoxysilane, 3-mercaptopropyl tri-isopropoxysilane; 3-mercaptopropyl trioctoxysilane, 2-mercaptoethyl tri(2'-ethylhexoxy)silane, 2-mercaptoethyl dimethoxy ethoxysilane, 3-mercaptopropyl methoxyethoxypropoxysilane, 3-mercaptopropyl dimethoxy methylsilane, 3-mercaptopropyl methoxy dimethylsilane, 3-mercaptopropyl ethoxy dimethylsilane, 3-mercaptopropyl diethoxy methylsilane, 3-mercaptopropyl cyclohexoxy dimethyl silane, 4-mercaptobutyl trimethoxysilane, 3-mercapto-3-methylpropyltrimethoxysilane, 3-mercapto-3-methylpropyl-tripropoxysilane, 3-mercapto-3-ethylpropyl-dimethoxy methylsilane, 3-mercapto-2-methylpropyl trimethoxysilane, 3-mercapto-2-methylpropyl dimethoxy phenylsilane, 3-mercaptocyclohexyl-trimethoxysilane, 12-mercaptododecyl trimethoxy silane, 12-mercaptododecyl triethoxy silane, 18-mercaptooctadecyl trimethoxysilane, 18-mercaptooctadecyl methoxydimethylsilane, 2-mercapto-2-methylethyl-tripropoxysilane, 2-mercapto-2-methylethyl-trioctoxysilane, 2-mercaptophenyl trimethoxysilane, 2-mercaptophenyl triethoxysilane; 2-mercaptotolyl trimethoxysilane; 2-mercaptotolyl triethoxysilane; 1-mercaptomethyltolyl trimethoxysilane; 1-mercaptomethyltolyl triethoxysilane; 2-mercaptoethylphenyl trimethoxysilane; 2-mercaptoethylphenyl triethoxysilane; 2-mercaptoethyltolyl trimethoxysilane; 2-mercaptoethyltolyl triethoxysilane; 3-mercaptopropylphenyl trimethoxysilane; 3-mercaptopropylphenyl triethoxysilane; 3-mercaptopropyltolyl trimethoxysilane; and 3-mercaptopropyltolyl triethoxysilane.

8. The process of claim 1 wherein said organic solvent is toluene.

9. The process of claim 1 wherein the reaction is conducted at a temperature ranging from 10° C. to 140° C.

10. The process of claim 9 wherein the reaction is conducted at a temperature ranging from 20° C. to 90° C.

11. The process of claim 1 wherein the reaction is conducted at a pressure ranging from 0.096 to 4.83 kg/cm$^2$.

* * * * *